(12) United States Patent
Hintermann et al.

(10) Patent No.: US 7,432,293 B2
(45) Date of Patent: Oct. 7, 2008

(54) HETEROCYCLIC COMPOUNDS USEFUL AS NURR-1 ACTIVATORS

(75) Inventors: Samuel Hintermann, Basel (CH); Bastian Hengerer, Ulm (DE); Boris Schmidt, Grenzach (DE)

(73) Assignee: Novartis AG, Basel (CH)

( * ) Notice: Subject to any disclaimer, the term of this patent is extended or adjusted under 35 U.S.C. 154(b) by 484 days.

(21) Appl. No.: 10/545,245

(22) PCT Filed: Feb. 13, 2004

(86) PCT No.: PCT/EP2004/001372

§ 371 (c)(1),
(2), (4) Date: Aug. 12, 2005

(87) PCT Pub. No.: WO2004/072050

PCT Pub. Date: Aug. 26, 2004

(65) Prior Publication Data

US 2006/0089365 A1 Apr. 27, 2006

(30) Foreign Application Priority Data

Feb. 14, 2003 (GB) ................... 0303503.7

(51) Int. Cl.
*A61K 31/42* (2006.01)
*A61K 31/4245* (2006.01)
*C07D 263/30* (2006.01)
*C07D 271/06* (2006.01)

(52) U.S. Cl. .............. 514/364; 548/125; 548/131; 548/215; 548/235; 548/236; 514/361; 514/374

(58) Field of Classification Search ............ 548/125, 548/131, 215, 235, 236; 514/361, 364, 374
See application file for complete search history.

(56) References Cited

U.S. PATENT DOCUMENTS 6,255,327 B1   7/2001  Brenner et al.
6,277,872 B1   8/2001  Brenner et al.
6,545,009 B1 * 4/2003  Sugiyama et al. ........... 514/277
7,223,791 B2 * 5/2007  Maekawa et al. ........... 514/461

FOREIGN PATENT DOCUMENTS

EP        0 504 574        9/2002

* cited by examiner

Primary Examiner—Golam M Shameem
(74) Attorney, Agent, or Firm—Mark W. Milstead

(57) ABSTRACT

The present invention relates to compounds of formula (I): wherein $R_1$ is hydroxy, $C_{1-4}$ alkoxy, amino, $C_{1-4}$ alkyl-amino, di $C_{1-4}$ alkylamino, benzyloxy or $C_2$-$C_7$ alkanoyl, $R_2$ is $C_{1-4}$ alkyl, $C_{1-4}$ alkoxy, $C_{1-4}$ alkoxy $C_{1-4}$ alkoxy, $CF_3$, halogen, $C_{1-4}$ alkylamino, di $C_{1-4}$ alkylamino, di $C_{1-4}$ alkylamino $C_{1-4}$ alkoxy or N—$C_{1-4}$ alkoxy $C_{1-4}$ alkyl-N—$C_{1-4}$ alkylamino, N—$C_{1-4}$ alkyl-piperazinyl, morpholinyl or pyrrolidinyl-$C_{1-4}$ alkoxy, wherein the $C_{1-4}$ alkyl radicals in $R_2$ are optionally further substituted by $C_{1-4}$ alkyl, halogen, cyano, amino, alkoxy or alkylthio, X is N or O, Y is N, O or CH, Z is N or CH, and W is N or CH, provided that (a) $R_1$ is not hydroxy or $C_{1-4}$ alkoxy when $R_2$ is $CF_3$, X is O, Y is CH, Z is N and W is CH, (b) $R_1$ is not hydroxy or $C_{1-4}$ alkoxy when $R_2$ is $CF_3$ or chloro, X is N, Y is O, Z is CH and W is CH, (c) $R_1$ is not hydroxy when $R_2$ is $CF_3$, X is O, Y is N, Z is CH and W is CH and (d) X and Y are not simultaneously O, the salts thereof; their preparation, their use and pharmaceutical compositions containing them.

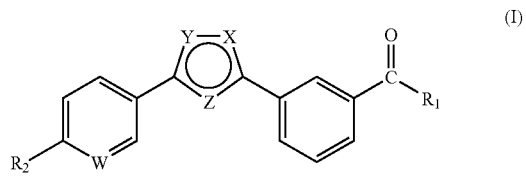

(I)

6 Claims, No Drawings

HETEROCYCLIC COMPOUNDS USEFUL AS NURR-1 ACTIVATORS

The present invention relates to heterocyclic compounds useful as Nurr-1 activators, their preparation, their use and pharmaceutical compositions containing them.

The invention provides compounds of formula I

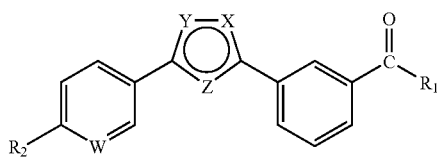

wherein
- $R_1$ is hydroxy, $C_{1-4}$alkoxy, amino, $C_{1-4}$alkyl-amino, di $C_{1-4}$alkylamino, benzyloxy or $C_2$-$C_7$alkanoyl,
- $R_2$ is $C_{1-4}$alkyl, $C_{1-4}$alkoxy, $C_{1-4}$alkoxy$C_{1-4}$alkoxy, $CF_3$, halogen, $C_{1-4}$alkylamino, di $C_{1-4}$alkylamino, di $C_{1-4}$alkylamino $C_{1-4}$alkoxy or N—$C_{1-4}$alkoxy $C_{1-4}$alkyl-N—$C_{1-4}$alkylamino, N—$C_{1-4}$alkyl-piperazinyl, morpholinyl, pyrrolidinyl-$C_{1-4}$alkoxy, wherein the $C_{1-4}$alkyl radicals in $R_2$ are optionally further substituted by $C_{1-4}$alkyl, halogen, cyano, amino, alkoxy or alkylthio,
- X is N or O,
- Y is N, O or CH,
- Z is N or CH, and
- W is N or CH,
- provided that (a) $R_1$ is not hydroxy or $C_{1-4}$alkoxy when $R_2$ is $CF_3$, X is O, Y is CH, Z is N and W is CH, (b) $R_1$ is not hydroxy or $C_{1-4}$alkoxy when $R_2$ is $CF_3$ or chloro, X is N, Y is O, Z is CH and W is CH, (c) $R_1$ is not hydroxy when $R_2$ is $CF_3$, X is O, Y is N, Z is CH and W is CH and (d) X and Y are not simultaneously O, and their salts.

Any alkyl or alkoxy group as defined above preferably has one or two carbon atoms and more preferably is methyl or methoxy.

The $C_{1-4}$alkyl radicals in $R_2$ are optionally further substituted by $C_{1-4}$alkyl, halogen, cyano, amino, alkoxy or alkylthio. Preferably, such $C_{1-4}$alkyl radicals in $R_2$ are not further substituted.

$C_2$-$C_7$alkanoyl is preferably $C_{1-4}$alkyl-CO—$CH_2$—O—.

Halogen denotes fluorine, chlorine or bromine.

The present invention in particular relates to compounds of formula I wherein
- $R_1$ is hydroxy, $C_{1-4}$alkoxy, amino, $CH_3$—CO—$CH_2$—O— or $C(CH_3)_3$—CO—$CH_2$—O—,
- $R_2$ is $C_{1-4}$alkoxy, $C_{1-4}$alkoxy$C_{1-4}$alkoxy, $CF_3$, halogen, di $C_{1-4}$alkylamino, di $C_{1-4}$alkylamino $C_{1-4}$alkoxy or N—$C_{1-4}$alkoxy $C_{1-4}$alkyl-N—$C_{1-4}$alkylamino,
- X is N or O,
- Y is N, O or CH
- Z is N or CH, and
- W is N or CH,
- provided that (a) $R_1$ is not hydroxy or $C_{1-4}$alkoxy when $R_2$ is $CF_3$, X is O, Y is CH, Z is N and W is CH, (b) $R_1$ is not hydroxy or $C_{1-4}$alkoxy when $R_2$ is $CF_3$ or chloro, X is N, Y is O, Z is CH and W is CH, (c) $R_1$ is not hydroxy when $R_2$ is $CF_3$, X is O, Y is N, Z is CH and W is CH and (d) X and Y are not simultaneously O.

In one preferred embodiment of the invention, X is O, Y is N and Z is N.

In another preferred embodiment of the invention, X is O, Y is CH and Z is N.

In a further preferred embodiment of the invention, X is N, Y is O and Z is CH.

In a further preferred embodiment of the invention, X is O, Y is N and Z is CH.

In a further aspect, the invention provides a process for the production of the compounds of formula I and their salts, comprising the step of a) for producing a compound of formula I wherein X is O, Y is N and Z is N, reacting a compound of formula II

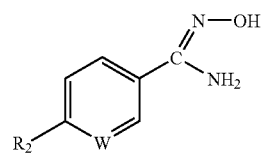

wherein $R_2$ and W are as defined above, with a compound of formula III

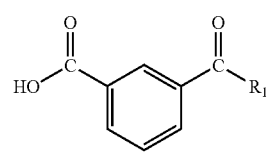

wherein $R_1$ is as defined above, or b) for producing a compound of formula I wherein X is O, Y is CH and Z is N, reacting a compound of formula IV

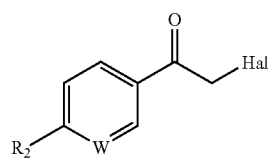

wherein $R_2$ and W are as defined above and Hal is halogen, with a compound of formula III, or c) for producing a compound of formula I wherein X is O, Y is N and W is CH, reacting a compound of formula V

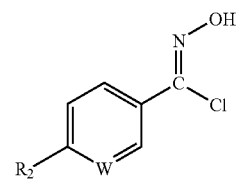

wherein $R_2$ and W are as defined above, with a compound of formula VI

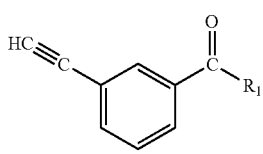

wherein $R_1$ is as defined above, or d) for producing a compound of formula I wherein X is N, Y is O and W is CH, reacting a compound of formula VII

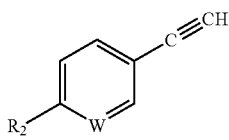

wherein $R_2$ and W are defined above, with a compound of formula VIII

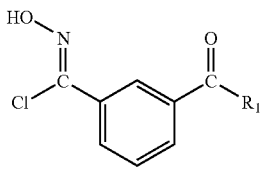

wherein $R_1$ is as defined above.

The reactions can be effected according to known methods, for example as described in Example 1 for the reaction under a), as described in Example 6 for the reaction under b), as described in Example 10 for the reaction under c) and as described in Example 14 for the reaction under d).

Compounds of formula I wherein $R_1$ is amino can be produced from the corresponding compounds wherein $R_1$ is hydroxy, by amide formation according to conventional procedures, e.g. as described in Example 5. Compounds of formula I wherein $R_1$ is $CH_3$—CO—$CH_2$—O— or $C(CH_3)_3$—CO—$CH_2$—O— can be produced from the corresponding compounds wherein $R_1$ is hydroxy, by reaction with 1-chloro-propan-2-one or 1-bromo-3,3-dimethyl-butan-2-one, respectively, according to conventional procedures, e.g. as described in Example 6.

Working up the reaction mixtures and purification of the compounds thus obtained may be carried out in accordance to known procedures.

Salts may be produced from the free compounds in known manner, and vice-versa.

The starting compounds of formulae II, III, IV, V, VI, VII and VIII are known or may be produced in analogous manner to known procedures.

Compounds of formula I and their pharmaceutically acceptable salts, hereinafter referred to as agents of the invention, exhibit valuable pharmacological properties where tested in vitro using Nurr1 expressing cell cultures and in vivo, and are therefore useful as pharmaceuticals.

The nuclear receptor Nurr1 is known to be causally involved in the functional differentiation of midbrain dopaminergic neurones both during development and in adult animals. The defects of dopaminergic neurones observed in the ventral midbrain of Nurr1 knockout animals resemble the pattern of neuronal degeneration in Parkinson's disease, in which the primary motor defects are caused by the degeneration of the substantia nigra dopaminergic system (Zetterström et al., 1997; Castillo et al., 1998 and Saucedo-Cardenas et al., 1998). Nurr1 activators are therefore suggested for preventing or delaying the onset of Parkinsonian symptoms.

The affinity of the agents of the invention to the Nurr1 receptor can be determined in vitro in binding studies:

Two-dimensional $^1H$-$^{15}N$ correlated spectra (HSQC) are recorded of uniformly $^{15}N$-labeled ligand binding domain (LBD) of Nurr1 expressed in *E. Coli*. The spectra provide a fingerprint of the protein structure and changes in the exact positions of some of the cross peaks in the 2-d spectrum upon titration of a compound indicate ligand binding.

In this assay, changes in chemical shift are observed in some peaks at concentrations of 300 μM of the agent of the invention, using 50 μM uniformly $^{15}N$-labeled Nurr1 LBD.

The activity of the agents of the invention at the Nurr1 receptor can be determined in vitro in cellular assays:

Induction of the biological activity of the Nurr1 receptor by the agents of the invention can be measured by the transactivation of a Nurr1 responsive reporter gene in a midbrain dopaminergic cell line. The assay is based on the transcription promoting effect of Nurr1. The reporter gene can be activated both by Nurr1 monomers and Nurr1/RXR heterodimers. RXR is a frequent heterodimerisation partner of nuclear receptors and it has been shown that Nurr1 can form heterodimers with RXR (Zetterström R H et al. Mol. Endocrinol. 1996; 10:1656-1666).

In this assay the agents of the invention significantly increase the reporter gene activity dose dependently at $EC_{50}$s of about 1 to about 1000 nM.

In vivo, the agents of the invention significantly increase midbrain dopamine levels at doses of 5 to 30 mg/kg p.o. in the following assay:

OF1 mice are treated with the test compound for five days and sacrificed 5 hours after the last compound application. Dopamine levels are measured in substantia nigra and striatal tissue punches. 10 animals are treated in each group.

The agents of the invention are therefore useful in the treatment of Parkinson's disease.

Additionally, several compounds of formula I can act as pro-drugs of other compounds of formula I, e.g. a compound wherein $R_1$ is $C_{1-4}$ alkoxy or benzyloxy might be hydrolyzed under physiological to some extent to a corresponding compound of formula I wherein $R_1$ is hydroxy. Hence, in a broader sense, the present invention embraces also pro-drugs of the compounds of formula I.

For the above-mentioned indication, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 500, preferably from about 0.5 to about 100 mg/kg animal body weight. In larger mammals, for example humans, an indicated daily dosage is in the range from about 1 to about 500, preferably from about 1 to about 300 mg of an agent of the invention, conveniently administered, for example, in divided doses up to four times a day or in sustained release form.

The agents of the invention may be administered in free form or in pharmaceutically acceptable salt form. Such salts may be prepared in conventional manner and exhibit the same order of activity as the free compounds.

The agent of the invention may be administered by any conventional route, in particular enterally, preferably orally, for example in the form of tablets or capsules, or parenterally, for example in the form of injectable solutions or suspensions.

The agents of the invention may alternatively be administered e.g. topically in the form of a cream, gel or the like, or by inhalation, e.g. in dry powder form.

Examples for compositions comprising an agent of the invention include, e.g. a solid dispersion, an aqueous solution, e.g. containing a solubilising agent, a microemulsion and a suspension of an agent of the invention. The composition may be buffered to a pH in the range of e.g. from 3.5 to 9.5, by a suitable buffer.

The agents of the invention can be administered either alone or in combination with other pharmaceutical agents effective in the treatment of Parkinson's disease.

Thus, the agents of the invention can be used for the treatment of Parkinson's disease in combination with, for example, dopamine precursors (e.g. different levodopa preparations), dopamine agonists (e.g. Bromocriptine, Pramipexole), catechol-O-methyltransferase inhibitors (e.g. Entacapone, Tolcapone), monoamine oxidase B inhibitors (e.g. Selegiline), NMDA antagonists (e.g. Amantadine) and anticholinergics (e.g. Biperiden, Orphenedrine).

In accordance with the foregoing, the present invention also provides the use of an agent of the invention, for the manufacture of a medicament for the treatment of Parkinson's disease.

The present invention furthermore provides a pharmaceutical composition comprising a novel compound of formula I in free base or pharmaceutically acceptable acid addition salt form, in association with at least one pharmaceutical carrier or diluent. Such compositions may be manufactured in conventional manner. Unit dosage forms contain, for example, from about 0.25 to about 150, preferably from 0.25 to about 25 mg of the compound.

The pharmaceutical compositions for separate administration of the combination partners and for the administration in a fixed combination, i.e. a single galenical composition comprising at least two combination partners according to the invention, can be prepared in a manner known per se and are thus suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

In particular, a therapeutically effective amount of each of the combination partners may be administered simultaneously or sequentially and in any order, and the components may be administered separately or as fixed combination.

Accordingly the invention also provides a combination comprising a therapeutically effective amount of a novel compound of formula I in free base or pharmaceutically acceptable acid addition salt form and a second drug substance, said second drug substance being for example for use in Parkinson's disease.

Moreover the present invention provides the use of a novel compound of formula I in free base or pharmaceutically acceptable acid addition salt form, as pharmaceutical for the treatment of Parkinson's disease.

In still a further aspect the present invention provides a method for the treatment of Parkinson's disease in a subject in need of such treatment, which comprises administering to such subject a therapeutically effective amount of a novel compound of formula I in free base or pharmaceutically acceptable acid addition salt form.

The following examples illustrate the invention.

EXAMPLE 1

3-[3-(4-Fluoro-phenyl)-[1,2,4]oxadiazol-5-yl]-benzoic acid a) 4-Fluoro-N-hydroxy-benzamidine In a 50 ml round bottom flask, 3.0 g (24.8 mmol) of 4-fluoro-benzonitrile are suspended in 50 ml of ethanol and 1.46 ml of aqueous hydroxylamine (50%, 24.8 mmol) are added. The mixture is heated to 90° C. and the resulting solution stirred at this temperature for 16 h. After cooling to room temperature, the solvent is removed in vacuo and the resulting residue recrystallised from 25 ml of ethanol/water (1:5) which yields a white solid. Mass spectrum: m/z $(M+H)^+$: 155.0 b) 3-[3-(4-Fluoro-phenyl)-[1,2,4]oxadiazol-5-yl]-benzoic acid methyl ester

In a 50 ml flask, 1.17 g (6.5 mmol) of isophtalic acid monomethyl ester are dissolved in 10 ml of DMF. To this solution, 1.16 g (7.2 mmol, 1.1 eq.) of 1,1'-carbonyl-diimidazole is added at room temperature under nitrogen. The mixture is stirred until carbon dioxide formation stops. Then, 1.00 g (6.5 mmol) of 4-fluoro-N-hydroxy-benzamidine is added and the resulting yellow solution stirred for 2 h. Now, another 1.16 g (7.2 mmol, 1.1 eq.) of 1,1'-carbonyl-diimidazole are added and the mixture is heated to 115° C. After 2 h at this temperature, the reaction mixture is cooled to room temperature and the solvent removed in vacuo. After chromatographical purification (160 g $SiO_2$; eluent: hexane/$CH_2Cl_2$ 6:4 to 1:1) the title compound is obtained as a white solid. Mass spectrum: m/z $(M+H)^+$: 299.0 c) 3-[3-(4-Fluoro-phenyl)-[1,2,4]oxadiazol-5-yl]-benzoic acid

In a 25 ml flask, 0.93 g (3.1 mmol) of 3-[3-(4-fluoro-phenyl)-[1,2,4]oxadiazol-5-yl]-benzoic acid methyl ester are dissolved in 17 ml of dioxane. Then, 4.7 ml of an aqueous lithium hydroxide solution (1M, 4.7 mmol, 1.5 eq.) are added and the cloudy mixture is stirred for 6 h at room temperature. Now, the dioxane is removed in vacuo, 20 ml of water are added and the pH of the solution is adjusted to 2. The resulting precipitate is filtered and washed with water and $CH_2Cl_2$. This yields, after drying, the title compound. Mass spectrum: m/z $(M-H)^-$: 283.0

According to the procedure described for Example 1, using the appropriate nitrile, the following compounds are prepared:

EXAMPLE 2

3-[3-(4-Trifluoromethyl-phenyl)-[1,2,4]oxadiazol-5-yl]-benzoic acid: This compound is obtained using 4-trifluoromethyl-benzonitrile as a white solid. Mass spectrum: m/z $(M-H)^-$: 333.0

EXAMPLE 3

3-{3-[4-(2-Methoxy-ethoxy)-phenyl]-[1,2,4]oxadiazol-5-yl}-benzoic acid: This compound is obtained using 4-(2-methoxy-ethoxy)-benzonitrile as a white solid. Mass spectrum: m/z $(M+H)^+$: 341.0

EXAMPLE 4

3-{3-[4-(2-Dimethylamino-ethoxy)-phenyl]-[1,2,4]oxadiazol-5-yl}-benzoic acid: This compound is obtained using 4-(2-dimethylamino-ethoxy)-benzonitrile as a white solid. Mass spectrum: m/z (M+H)$^+$: 354.2

EXAMPLE 5

3-[3-(6-Methylamino-pyridin-3-yl)-[1,2,4]oxadiazol-5-yl]-benzoic acid: This compound is obtained using 6-methylamino-nicotinonitrile as a white solid. Mass spectrum: m/z (M+H)$^+$: 311.0

EXAMPLE 6

3-(3-p-Tolyl-[1,2,4]oxadiazol-5-yl)-benzoic acid: This compound is obtained using p-tolyl-benzonitrile as a white solid. Mass spectrum: m/z (M–H)$^-$: 279.0

EXAMPLE 7

3-[3-(4-Chloro-phenyl)-[1,2,4]oxadiazol-5-yl]-benzoic acid: This compound is obtained using 4-chloro-benzonitrile as a white solid. Mass spectrum: m/z (M+H)$^+$: 301.0

EXAMPLE 8

3-{3-[4-(4-Methyl-piperazin-1-yl)-phenyl]-[1,2,4]oxadiazol-5-yl}-benzoic acid: This compound is obtained using 4-(4-methyl-piperazin-1-yl)-benzonitrile as a white solid. Mass spectrum: m/z (M+H)$^+$: 365.1

EXAMPLE 9

3-{3-[4-(2-Pyrrolidin-1-yl-ethoxy)-phenyl]-[1,2,4]oxadiazol-5-yl}-benzoic acid: This compound is obtained using 4-(2-pyrrolidin-1-yl-ethoxy)-benzonitrile as a white solid. Mass spectrum: m/z (M+H)$^+$: 380.1

EXAMPLE 10

3-[3-(4-Methoxy-phenyl)-[1,2,4]oxadiazol-5-yl]-benzoic acid: This compound is obtained using 4-methoxy-benzonitrile as a white solid. Mass spectrum: m/z (M+H)$^+$: 311.1

EXAMPLE 11

3-[3-(6-Dimethylamino-pyridin-3-yl)-[1,2,4]oxadiazol-5-yl]-benzoic acid a) 6-Dimethylamino-nicotinonitrile In a 25 ml sealed tube, 1.0 g (7.2 mmol) of 6-chloro-nicotino-nitrile and 1.9 ml (10.8 mmol, 5.6 M, 1.5 eq.) of a solution of dimethyl-amine in ethanol are dissolved in 10 ml of THF. Then, 1.5 ml (10.8 mmol, 1.5 eq.) of triethyl-amine are added and the reaction mixture heated to 75° C. After 4 h, the mixture was cooled to rt and concentrated. The residue was taken up in dichloro-methane and aqueous NaHCO3 (5%), the phases separated and the aqueous phases extracted two times with dichloro-methane. The combined organic phases were dried (Na2SO4) and concentrated. The title compound was obtained as a beige solid and used for the next step without further purification. Mass spectrum: m/z (M+H)$^+$: 148.0 b) 6-Dimethylamino-N-hydroxy-nicotinamidine

In a 100 ml round flask, 4.7 g (31.9 mmol) of 6dimethylamino-nicotinonitrile and 1.88 ml (31.9 mmol) of aqueous hydroxylamine (50%) are dissolved in 25 ml of ethanol. This mixture is reacted at 90° C. for 6 h. Then another 0.45 ml (8.1 mmol, 0.25 eq.) of hydroxylamine-solution is added. After 11 h at 90° C., the mixture is cooled and the solvent removed in vacuo. This yields the title compound as light yellow solid, which is used for the next step without purification. Mass spectrum: m/z (M+H)$^+$: 181.0 c) 3-[3-(6-Dimethylamino-pyridin-3-yl)-[1,2,4]oxadiazol-5-yl]-benzoic acid methyl ester In a 50 ml round flask, a mixture of 5.6 (31.1 mmol) of isophtalic acid monomethyl ester and 6.71 g (34.2 mmol, 1.1 eq.) of carbonyl-diimidazole is stirred for 1 h at rt. Then, 5.60 g (31.1 mmol) of 6-dimethylamino-N-hydroxy-nicotinamidine is added and the resulting mixture stirred for another 3 h. After completion of the reaction, the solvent is removed. The resulting residue is suspended in water, vigorously stirred and then filtered. The obtained solid is washed two times with diethyl-ether and dried. This yields 10.0 g (94%) of a light yellow solid. Mass spectrum: m/z (M+H)$^+$: 343.1 The crude intermediate (9.8 g (28.7 mmol) is then redissolved in 200 ml of THF and 1.81 g (5.7 mmol, 0.2 eq.) of tetrabutyl-ammonium fluoride tri-hydrate TBAF) is added. After 1.5 h, another 0.2 eq. of TBAF is and the mixture stirred at rt for 20 h. Then, solvent is removed under vacuo, and the residue taken up in 200 ml of dichloro-methane and washed twice with NaHCO3 (5%). The combined aqueous phases are extracted three times with dichloro-methane, the combined organic phases dried (Na2SO4) and concentrated. This yields the title compound as light yellow solid, which is used for the next step without purification. Mass spectrum: m/z (M+H)$^+$: 325.2 d) 3-[3-(6-Dimethylamino-pyridin-3-yl)-[1,2,4]oxadiazol-5-yl]-benzoic acid

In a 250 ml round flask, 7.0 g (21.6 mmol) of 3-[3-(6-dimethylamino-pyridin-3-yl)-[1,2,4]oxadiazol-5-yl]-benzoic acid methyl ester is dissolved in 150 ml of dioxane and treated with 32.4 ml (1M, 32.4 mmol, 1.5 eq.) of aqueous LiOH solution. After 20 h, the solvent is removed under vacuo and the residue suspended in 300 ml H2O. The pH value is then adjusted to 2 by addition of 1M HCl-solution. The precipitate is stirred for 30 minutes, then filtered, washed with 0.1 M HCl-solution and with diethyl-ether and dried. This yields the title compound as light yellow solid. Mass spectrum: m/z (M+H)$^+$: 311.0

EXAMPLE 12

3-{3-[4-(2-Methoxy-ethoxy)-phenyl]-[1,2,4]oxadiazol-5-yl}-benzamide: In a 50 ml round flask, 750 mg (2.2 mmol) of 3-{3-[4-(2-methoxy-ethoxy)-phenyl]-isoxazol-5-yl}-benzoic acid are suspended in 7.5 ml of dichloroethane. Then, 17 µl (0.22 mmol, 0.1 eq.) of DMF and 0.18 ml (2.42 mmol, 1.1 eq.) of thionyl-chloride are added at room temperature. The reaction mixture is then heated to 70° C. After 2 h, another 81 µl (1.1 mmol, 0.5 eq.) of thionyl-chloride is added. After another hour, the clear solution is concentrated in vacuo. The resulting oil is taken up in 7.5 ml of methanolic ammonia (2M) and the suspension stirred for 1.5 h. Then, the mixture is filtered and the product dried which yields the title compound as white solid. Mass spectrum: m/z (M+H)$^+$: 340.0

EXAMPLE 13

3-[4-(4-Chloro-phenyl)-oxazol-2-yl]-benzoic acid a) Isophthalic acid mono-[2-(4-chloro-phenyl)-2-oxo-ethyl] ester

In a 25 ml round flask, 2.0 g (11.1 mmol) of isophtalic acid monomethyl ester and 2.6 g (11.1 mmol) 2-bromo-1-(4-chloro-phenyl)-ethanone are dissolved in 10 ml of DMF followed by addition of 3.1 g (22.2 mmol, 2.0 eq.) of $K_2CO_3$. After stirring the suspension 2 h at room temperature, the solvent is removed in vacuo and the residue taken up in $CH_2Cl_2$. The organic phase is washed with aqueous $NaHCO_3$ (5%) and the phases separated. The organic layer is dried ($Na_2SO_4$) and concentrated to yield the title compound which is used for the next step without further purification. Mass spectrum: m/z $(M+H+NH_3)^+$: 198.0 b) 3-[4-(4-Chloro-phenyl)-oxazol-2-yl]-benzoic acid methyl ester

In a 25 ml flask, 1.71 g (4.9 mmol) of isophthalic acid mono-[2-(4-chloro-phenyl)-2-oxo-ethyl] ester are dissolved in 10 ml of acetic acid. To this solution, 2.96 g (49.3 mmol, 10 eq.) of urea is added and the mixture heated to 140° C. After 6 h at this temperature, the reaction mixture is cooled to room temperature and the mixture is poured onto water. The pH is carefully adjusted to 8 by addition of saturated $Na_2CO_3$-solution and then the mixture is extracted three times with ethyl acetate. The combined organic phases are dried ($Na_2SO_4$) and concentrated. After chromatographical purification (eluent:hexane/ethyl acetate 19:1 to 13:7), the title compound is obtained together with the corresponding imidazole derivative (0.11 g, 7%). Mass spectrum: m/z $(M+H)^+$: 314.2; 316.0 c) 3-[4-(4-Chloro-phenyl)-oxazol-2-yl]-benzoic acid

In a 25 ml flask, 0.11 g (0.36 mmol) of 3-[4-(4-chloro-phenyl)-oxazol-2-yl]-benzoic acid methyl ester are dissolved in 5 ml of dioxane. Then, 0.72 ml of an aqueous lithium hydroxide solution (1M, 0.72 mmol, 2.0 eq.) are added and the mixture is stirred for 20 h at room temperature. Now, the pH of the solution is adjusted to 2 by drop wise addition of hydrochloric acid (4M). The resulting precipitate is filtered and washed with water. This yields, after drying, the title compound as a white solid. Mass spectrum: m/z $(M+H)^+$: 300.1; 302.2

According to the procedure described for Example 13, using the appropriate 2-bromo-ethanone, the following compounds are prepared:

EXAMPLE 14

3-[4-(4-Methoxy-phenyl)-oxazol-2-yl]-benzoic acid: This compound is obtained using 2-bromo-1-(4-methoxy-phenyl)-ethanone as a white solid. Mass spectrum: m/z $(M+H)^+$: 296.2

EXAMPLE 15

3-[4-(4-Bromo-phenyl)-oxazol-2-yl]-benzoic acid: This compound is obtained using 2-bromo-1-(4-bromo-phenyl)-ethanone as a white solid. Mass spectrum: m/z $(M+H)^+$: 343.9, 345.9

EXAMPLE 16

3-[4-(4-Fluoro-phenyl)-oxazol-2-yl]-benzoic acid: This compound is obtained using 2-bromo-1-(4-fluoro-phenyl)ethanone as a white solid. Mass spectrum: m/z $(M+H)^+$: 284.0

EXAMPLE 17

3-(5-p-Tolyl-isoxazol-3-yl)-benzoic acid a) 3-(Hydroxyimino-methyl)-benzoic acid methyl ester

In a 100 ml round flask, 2.31 g (14.1 mmol) of 3-formyl-benzoic acid methyl ester are dissolved in 25 ml of water and 45 ml of methanol and cooled to 0° C. After reaching this temperature, 980 mg (14.1 mmol) of hydroxylamine hydrochloride are added and the mixture stirred for 1 h under warming to room temperature. Then, the mixture is poured onto water and extracted twice with ethyl acetate. The organic layers are dried with brine and over $Na_2SO_4$ and concentrated. This yields the title compound as a white solid which is used for the next step without purification. Mass spectrum: m/z $(M+H)^+$: 179.9 b) 3-[Chloro-(hydroxyimino)-methyl]-benzoic acid methyl ester

In a 50 ml round flask, 2.45 g (13.7 mmol) of 3-(hydroxy-imino-methyl)-benzoic acid methyl ester are dissolved in 13 ml of DMF. Then, 1.82 g (13.7 mmol) of N-chloro-succinimide are added in small portions in order to keep the reaction temperature below 40° C. After completion of the addition, the yellow mixture is stirred for 2 h at room temperature. The mixture is then poured onto water and extracted twice with diethyl ether. The combined organic layers are dried ($Na_2SO_4$) and concentrated under reduced pressure to remove remaining DMF-traces. This yields the title compound as a yellowish solid which is used for the next step without further purification. Mass spectrum: m/z $(M+H)^+$: 214.0; 216.0 c) 3-(5-p-Tolyl-isoxazol-3-yl)-benzoic acid methyl ester

In a 25 ml round flask, 1.9 g (8.9 mmol) of 3-[chloro-(hydroxyimino)-methyl]-benzoic acid methyl ester and 1.03 g (8.9 mmol) of 1-ethynyl-4-methyl-benzene are dissolved in 12 ml of $CHCl_3$ at 0° C. To this solution, 36 μl (0.4 mmol, 0.05 eq.) of pyridine and subsequently 1.24 ml (8.9 mmol) of triethyl amine are added and the mixture is stirred under warming to room temperature for 2 h. Then, the mixture is poured onto water, extracted twice with $CH_2Cl_2$, the organic layers are dried with brine and $Na_2SO_4$ and then concentrated. Chromatographic purification (250 g $SiO_2$; gradient elution, eluent: hexane/ethyl acetate 95:5→9:1) yields the title compound as a white solid. Mass spectrum: m/z $(M+H)^+$: 294.2 d) 3-(5-p-Tolyl-isoxazol-3-yl)-benzoic acid

In a 25 ml round flask, 330 mg (1.13 mmol) of 3-[5-p-tolyl-isoxazol-3-yl]-benzoic acid methyl ester is dissolved in 10 ml of dioxane and subsequently 1.69 ml of aqueous lithium hydroxide (1M, 1.69 mmol, 1.5 eq.) are added and the resulting solution stirred for 20 h at room temperature. Then, the dioxane is removed in vacuo, 10 ml of water are added and the pH adjusted to 2 with hydrochloric acid (1M). The precipitate is filtered and dried to yield the title compound as a white solid. Mass spectrum: m/z (M−H)+: 278.2

According to the procedure described for Example 17, the following compound is prepared:

EXAMPLE 18

3-[5-(6-Chloro-pyridin-3-yl)-isoxazol-3-yl]-benzoic acid: This compound is obtained using 2-chloro-5-ethynyl-pyridine as a white solid. Mass spectrum: m/z (M+H)+: 412.0

EXAMPLE 19

3-{5-[6-(Isobutyl-methyl-amino)-pyridin-3-yl]-isoxazol-3-yl}-benzoic acid: In a pressure tube, 200 mg (0.64 mmol) of 3-[5-(6-chloro-pyridin-3-yl)-isoxazol-3-yl]-benzoic acid, 97 mg (0.96 mmol, 1.5 eq.) of triethyl amine and 166 mg (1.9 mmol, 3.0 eq.) of isobutyl-methyl-amine are dissolved in 3 ml of THF. The reaction mixture is heated to 120° C. and after 6 h to 150° C. After 60 h, the mixture is cooled to room temperature and the solvent is removed. After addition of 10 ml of water, the pH is adjusted to 2 and the precipitate filtered off. The solid is then dissolved in 10 ml of methanol and 5 ml of dichloroethane, precipitated through addition of 10 ml of hexane and filtered. Recrystallisation from 15 ml of dichloromethane and 1 ml of methanol yields the title compound as a white solid. Mass spectrum: m/z (M+H)+: 352.2

According to the procedure described for Example 19, the following compound is prepared:

EXAMPLE 20

3-(5-{6[(2-Isopropoxy-ethyl)-methyl-amino]-pyridin-3-yl}-isoxazol-3-yl)-benzoic acid This compound is obtained using (2-isopropoxy-ethyl)-methyl-amine as a white solid. Mass spectrum: m/z (M+H)+: 382.2

EXAMPLE 21

3-[3-(4-Chloro-phenyl)-isoxazol-5-yl]-benzoic acid a) 3-[3-(4-Chloro-phenyl)-isoxazol-5-yl]-benzoic acid ethyl ester In a 10 ml round flask, 500 mg (2.9 mmol) of 3-ethynyl-benzoic acid ethyl ester and 652 mg (3.5 mmol, 1.2 eq.) of 4-chloro-N-hydroxy-benzenecarboximidoyl chloride are dissolved in 4 ml of CHCl$_3$. To this solution, 11 mg (0.14 mmol, 0.05 eq.) of pyridine and 290 mg (2.9 mmol) of triethyl amine are added at 0° C. under a nitrogen atmosphere. The orange solution is stirred under warming to room temperature for 20 h. The suspension is filtered and the solution concentrated in vacuo. Chromatographical purification (100 g SiO$_2$; eluent: hexane/ethyl acetate 9:1) yields the title compound as a white solid. Mass spectrum: m/z (M+H)+: 328.2; 330.2 b) 3-[3-(4-Chloro-phenyl)-isoxazol-5-yl]-benzoic acid

In a 25 ml round flask, 250 mg (0.76 mmol) of 3-[3-(4-chloro-phenyl)-isoxazol-5-yl]-benzoic acid ethyl ester are dissolved in 5 ml of dioxane. After addition of 1M aqueous lithium hydroxide (0.99 ml, 0.99 mmol, 1.3 eq.), the mixture is stirred at room temperature for 20 h. Then, the dioxane is removed in vacuo, 5 ml of water is added and the pH adjusted to 2 by addition of 1M hydrochloric acid. The precipitate is filtered off, washed with water and dried. This yields the title compound as a white solid. Mass spectrum: m/z (M−H)−: 298.1; 300.1

According to the procedure described for Example 21, the following compound is prepared:

EXAMPLE 22

3-{3-[4-(2-Methoxy-ethoxy)-phenyl]-isoxazol-5-yl}-benzoic acid: This compound is obtained using 4-(2-methoxy-ethoxy)-N-hydroxy-benzenecarboximidoyl chloride as a white solid. Mass spectrum: m/z (M+H)+: 340.1

EXAMPLE 23

3-{3-[4-(2-Methoxy-ethoxy)-phenyl]-isoxazol-5-yl}-benzoic acid 2-oxo-propyl ester: In a 25 ml round flask, 150 mg (0.44 mmol) of 3-{3-[4-(2-methoxy-ethoxy)-phenyl]-isoxazol-5-yl}-benzoic acid are dissolved. Then, 122 mg (0.88 mmol, 4 eq.) of K$_2$CO$_3$ and 49 mg (0.53 mmol, 1.2 eq.) of 1-chloro-propan-2-one are added and the suspension heated to 55° C. under nitrogen. After 48 h, the reaction is cooled to room temperature and the solvent evaporated. Chromatographic purification (10 g SiO$_2$; eluent: hexane/ethyl acetate 1:0 to 4:6) yields the title compound as a white solid. Mass spectrum: m/z (M+H)+: 396.0

According to the procedure described for Example 23, the following compound is prepared:

EXAMPLE 24

3-{3-[4-(2-Methoxy-ethoxy)-phenyl]-isoxazol-5-yl}-benzoic acid 3,3-dimethyl-2-oxo-butyl ester: This compound is obtained using 1-bromo-3,3-dimethyl-butan-2-one as a white solid. Mass spectrum: m/z (M+H)+: 438.0

The invention claimed is:
1. A compound of formula I

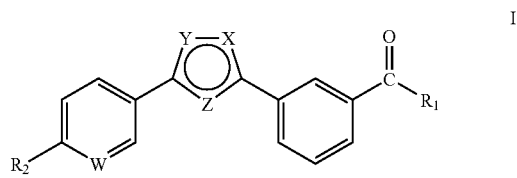

wherein
R$_1$ is hydroxy, C$_{1-4}$alkoxy, amino, C$_{1-4}$alkyl-amino, di C$_{1-4}$alkylamino, benzyloxy or C$_2$-C$_7$alkanoyl,
R$_2$ is C$_{1-4}$alkyl, C$_{1-4}$alkoxy, C$_{1-4}$alkoxyC$_{1-4}$alkoxy, CF$_3$, halogen, C$_{1-4}$alkylamino, di C$_{1-4}$alkylamino, di C$_{1-4}$alkylamino C$_{1-4}$alkoxy or N—C$_{1-4}$alkoxy C$_{1-4}$alkyl-N—C$_{1-4}$alkylamino, N—C$_{1-4}$alkyl-piperazinyl, morpholinyl or pyrrolidinyl-C$_{1-4}$alkoxy, wherein the C$_{1-4}$alkyl radicals in R$_2$ are optionally further substituted by C$_{1-4}$alkyl, halogen, amino, alkoxy or alkylthio,
X is N or O,
Y is N, O or CH,
Z is N or CH, and
W is N or CH,
provided that (a) R$_1$ is not hydroxy or C$_{1-4}$alkoxy when R$_2$ is CF$_3$, X is O, Y is CH, Z is N and W is CH, (b) R$_1$ is not hydroxy or C$_{1-4}$alkoxy when R$_2$ is CF$_3$ or chloro, X is N, Y is O, Z is CH and W is CH, (c) R$_1$ is not hydroxy when $R_2$ is $CF_3$, X is O, Y is N, Z is CH and W is CH and (d) X and Y are not simultaneously O,
and its salts.

2. The compound of formula I according to claim 1 wherein
$R_1$ is hydroxy, $C_{1-4}$alkoxy, amino, $C_{1-4}$alkyl-amino, di $C_{1-4}$alkylamino, benzyloxy or $C_2$-$C_7$alkanoyl,
$R_2$ is $C_{1-4}$alkyl, $C_{1-4}$alkoxy, $C_{1-4}$alkoxy$C_{1-4}$alkoxy, $CF_3$, halogen, $C_{1-4}$alkylamino, di $C_{1-4}$alkylamino, di $C_{1-4}$alkylamino $C_{1-4}$alkoxy or N—$C_{1-4}$alkoxy $C_{1-4}$alkyl-N—$C_{1-4}$alkylamino, N—$C_{1-4}$alkyl-piperazinyl, morpholinyl or pyrrolidinyl-$C_{1-4}$alkoxy,
X is N or O,
Y is N, O or CH,
Z is N or CH, and
W is N or CH,
provided that (a) $R_1$ is not hydroxy or $C_{1-4}$alkoxy when $R_2$ is $CF_3$, X is O, Y is CH, Z is N and W is CH, (b) $R_1$ is not hydroxy or $C_{1-4}$alkoxy when $R_2$ is $CF_3$ or chloro, X is N, Y is O, Z is CH and W is CH, (c) $R_1$ is not hydroxy when $R_2$ is $CF_3$, X is O, Y is N, Z is CH and W is CH and (d) X and Y are not simultaneously O,
and its salts.

3. The compound of formula I according to claim 1 wherein
$R_1$ is hydroxy, $C_{1-4}$alkoxy, amino, $CH_3$—CO—$CH_2$—O— or $C(CH_3)_3$—CO—$CH_2$—O—,
$R_2$ is $C_{1-4}$alkoxy, $C_{1-4}$alkoxy$C_{1-4}$alkoxy, $CF_3$, halogen, di $C_{1-4}$alkylamino, di $C_{1-4}$alkylamino $C_{1-4}$alkoxy or N—$C_{1-4}$alkoxy $C_{1-4}$alkyl-N—$C_{1-4}$alkylamino,
X is N or O,
Y is N, O or CH
Z is N or CH, and
W is N or CH,
provided that (a) $R_1$ is not hydroxy or $C_{1-4}$alkoxy when $R_2$ is $CF_3$, X is O, Y is CH, Z is N and W is CH, (b) $R_1$ is not hydroxy or $C_{1-4}$alkoxy when $R_2$ is $CF_3$ or chloro, X is N, Y is O, Z is CH and W is CH, (c) $R_1$ is not hydroxy when $R_2$ is $CF_3$, X is O, Y is N, Z is CH and W is CH and (d) X and Y are not simultaneously O,
and its salts.

4. A process for the preparation of a compound of formula I as defined in claim 1 or a salt thereof, comprising the step of
a) for producing a compound of formula I wherein X is O, Y is N and Z is N, reacting a compound of formula II

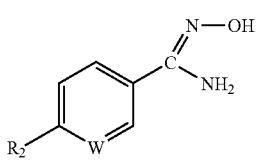

wherein $R_2$ and W are as defined in claim 1, with a compound of formula III

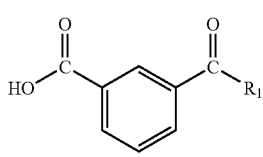

wherein $R_1$ is as defined in claim 1, or b) for producing a compound of formula I wherein X is O, Y is CH and Z is N, reacting a compound of formula IV

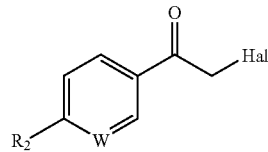

wherein $R_2$ and W are as defined in claim 1 and Hal is halogen, with a compound of formula III, or c) for producing a compound of formula I wherein X is O, Y is N and W is CH, reacting a compound of formula V

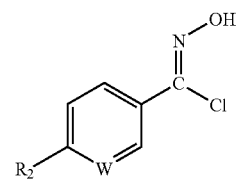

wherein $R_2$ and W are as defined in claim 1, with a compound of formula VI

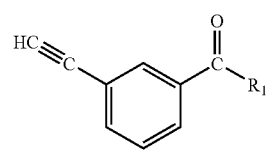

wherein $R_1$ is as defined in claim 1, or d) for producing a compound of formula I wherein X is N, Y is O and W is CH, reacting a compound of formula VII

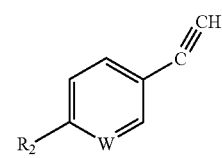

wherein $R_2$ and W are defined in claim 1, with a compound of formula VIII

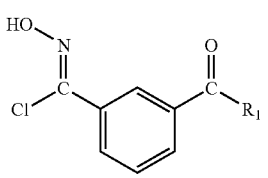

wherein $R_1$ is as defined in claim 1,
and recovering the resulting compound in free form or in form of a salt.

5. A pharmaceutical composition comprising a compound of claim 1 in free form or pharmaceutically acceptable salt form, in association with a pharmaceutical carrier or diluent.

6. A method for the treatment of Parkinson's disease in a subject in need of such treatment, which comprises administering to such subject a therapeutically effective amount of a compound of claim 1 in free form or pharmaceutically acceptable salt form.

* * * * *